United States Patent [19]
Hasegawa

[11] Patent Number: 5,190,456
[45] Date of Patent: Mar. 2, 1993

[54] AIR-DRIVEN DENTAL SCALER

[75] Inventor: Akiro Hasegawa, Tokyo, Japan

[73] Assignee: Micron Co., Ltd., Japan

[21] Appl. No.: 887,660

[22] Filed: May 26, 1992

Related U.S. Application Data

[63] Continuation of Ser. No. 370,120, Jun. 23, 1989, abandoned, which is a continuation of Ser. No. 99,385, Sep. 18, 1987, abandoned.

[30] Foreign Application Priority Data

Sep. 26, 1986 [EP] European Pat. Off. ......... 86113258.7

[51] Int. Cl.⁵ .............................................. A61C 1/07
[52] U.S. Cl. ..................................... 433/120; 433/118
[58] Field of Search ......................... 433/117, 118, 120

[56] References Cited

U.S. PATENT DOCUMENTS

| Re. 29,687 | 7/1978 | Sertich | 433/120 |
|---|---|---|---|
| 154,569 | 9/1874 | Straub | 433/120 |
| 2,960,314 | 11/1960 | Bodine, Jr. | 433/118 |
| 3,444,622 | 5/1969 | Mills et al. | 433/120 |
| 3,553,841 | 1/1971 | Austin, Jr. | 433/120 |
| 3,871,097 | 3/1975 | Melde | 433/120 |
| 4,289,486 | 9/1981 | Sargeant | 433/118 |
| 4,427,384 | 1/1984 | Sertich | 433/120 |
| 4,453,919 | 6/1984 | Takeshita | 433/120 |
| 4,484,892 | 11/1984 | Pernot et al. | 433/120 |
| 4,484,893 | 11/1984 | Finn | 433/120 |
| 4,634,376 | 1/1987 | Mossle et al. | 433/118 |

FOREIGN PATENT DOCUMENTS

| 60-55941 | 6/1978 | Japan . | |
|---|---|---|---|
| 56-83341 | 7/1981 | Japan . | |
| 56-166842 | 12/1981 | Japan . | |
| 59-25738 | 2/1984 | Japan . | |
| 0349626 | 10/1960 | Switzerland | 433/120 |

OTHER PUBLICATIONS

A

Primary Examiner—Cary E. O'Connor
Attorney, Agent, or Firm—Lorusso & Loud

[57] ABSTRACT

An air-driven dental scaler (10) having a scaler tip (78) oscillated by an air-driven vibrator (22) of the class wherein a disk-like rotor (40) is rotated within a disk-shaped chamber (38) to impart vibration to a vibrator body (26). In order to suppress or reduce annoying audible sound issued during operation of the dental scaler (10), the vibrator (22) is positioned immediately adjacent the distal end (24) of the casing (12) and the scaler tip (78) is directly mounted to the vibrator body (26), with the scaler tip (78) being unsupported by and vibrationally isolated from the casing (12) to enable the scaler tip (78) to oscillate without interference by the casing (12). This arrangement enables the frequency of vibration of the vibrating system (22/78) to increase to near the ultrasonic frequency range while retaining the full scaling capability of the dental scaler (10).

26 Claims, 7 Drawing Sheets

AIR-DRIVEN DENTAL SCALER

This application is a continuation of application Ser. No. 07/370,120, filed Jun. 23, 1989, now abandoned, which is a continuation of Ser. No. 07/099,385, filed Sep. 18, 1987, now abandoned.

TECHNICAL FIELD

This invention relates generally to a powered dental instrument and, more particularly, to an air-driven dental scaler for removing calculus or plaque from teeth.

BACKGROUND ART

Powered dental scalers commercially available on the market may generally be classified into two categories; electromechanical ultrasonic scalers, and air-driven subsonic scalers. The scalers of the former category may be grouped into those having magnetorestrictive oscillators and those having piezoelectric oscillators. Japanese Unexamined Patent Publication No. 59-25738, published Feb. 9, 1984; Japanese Unexamined Patent Publication No. 60-55941, published Apr. 1, 1985; and, Japanese Unexamined Utility Model Publication No. 53-71992 published Jun. 16, 1978, disclose examples of the prior art ultrasonic dental scalers with magnetorestrictive oscillators. The magnetorestrictive oscillator includes a coil winding and a magnetorestrictive transducer disposed within the winding. A high-frequency alternating current having a frequency in the range of about 20 to 40 kHz is supplied from a control unit to the coil winding to generate high-frequency alternating magnetic fields which induce ultrasonic acoustic vibrations in the magnetorestrictive transducer. The ultrasonic vibrations are transmitted through an acoustic coupling to a scaler tip to cause the tip to vibrate at an ultrasonic frequency. The piezoelectric oscillator, on the other hand, includes a piezoelectric transducer which is oscillated by a similar high-frequency alternating current applied thereon from a control unit. In both types of oscillators, the nature of the vibrations as generated in the transducer is acoustic, so that the sound waves or elastic waves generated therein are propagated axially through the transducer and through the acoustic coupling to the scaler tip to cause the scaler tip to vibrate at an ultrasonic frequency. Thus, the primary advantage of such electromechanical ultrasonic dental scalers, including magnetorestrictive or piezoelectric oscillator types, is that they are operable without producing an audible keen noise which would normally be encountered when the dentist is operating a turbine driven instrument, and which generally would have a considerably adverse affect on the feeling of a patient. Nevertheless, the electromechanical scalers have a disadvantage in that the control unit must be installed on or in the neighbourhood of the dental unit. The provision for such control unit also entails extra cost for the dentists.

Air-driven dental scalers are generally designed to be driven by a source of compressed air provided in an existing dental unit which is standard equipment in almost all dental clinics and, thus, have the advantage of being interchangeably usable in place of turbine-driven dental instruments by a simple connection to a flexible hose extending from the dental unit. Thus, there is no need for a separate control unit. Air-driven dental scalers includes various types of vibrators or oscillators. For example, U.S. Pat. No. Re. 29,687 reissued Jul. 4, 1978, describes a dental scaler having a central shaft resiliently supported adjacent both ends thereof by a casing. A sleeve-like rotor is rotatably mounted around the shaft at the center thereof and is adapted to be rotated by an offset jet of air to cause subsonic vibration of the shaft. The dental scaler disclosed in Japanese Unexamined Patent Publication No. 56-83341 published Jul. 7, 1981, employs a vibrator having a similar sleeve-like rotor rotatable around a shaft. Japanese Unexamined Patent Publication No. 56-166842 illustrates an air-driven dental scaler with another type of vibrator having an air turbine, the rotation of which is transformed by an eccentric to an oscillatory movement of a shaft coupled to the scaler tip.

Throughout these types of air-driven dental scalers, the mode of vibration of the vibrator shaft to which the scaler tip is mounted is entirely different from the mode of vibration encountered in the electromechanical dental scalers, wherein elastic waves oscillating at ultrasonic frequencies are generated in the magnetorestrictive or piezoelectric transducer and are axially transmitted to the scaler tip. For example, in the dental scaler described in U.S. Pat. No. Re. 29,687, the vibrator shaft carrying the scaler tip is resiliently supported adjacent the ends thereof by the casing of the scaler, and an external vibratory force is imparted from the rotating sleeve-like rotor at about the center of the shaft, so that the vibrator shaft undergoes flexural forced vibration, as opposed to elastic vibration, with the nodes of flexural vibration located at the points at which the shaft is supported by the casing. Obviously, the flexural nature of the mode of vibration has made it necessary to design the vibrator shaft to be long enough to cause the scaler tip to vibrate with a sufficient amplitude of vibration required for scaling. This has been a bar to increasing the frequency of vibration of the air-driven subsonic dental scalers to near to the ultrasonic range, the lower boundary of which is generally from 15 to 20 kHz. In fact, an annoying keen noise having a frequency of about 6,000 Hz has often been encountered in the prior art air-driven dental scalers referred to above. It appears to be taken for granted that the generation of audible sound or noise is inherent in the air-driven dental scalers, and that in the field of air-driven scalers, it is almost impossible to avoid annoying noise due to subsonic vibration. Obviously, no attempt has been hitherto made to improve the above described subsonic scalers in such a manner that the frequency thereof is increased to near to the ultrasonic frequency range.

Another type of air-driven dental scaler is described in U.S. Pat. No. 4,453,919 issued to Takeshita on Jun. 12, 1984 and assigned to the assignee of the present invention. This dental scaler comprises a unique air vibrator having a vibrator body defining a disk-like chamber in which a disk-like rotor is received. Compressed air from a source in the dental unit is injected into the chamber through tangential inlet ports or nozzles to generate in the chamber a swirling air stream that causes the rotor to rotate. Although it is not entirely clear how the vibration is generated in response to rotation of the rotor, the mechanism of the vibration is described by analogy to a wobbling coin spinning on a table surface, and striking that surface. In the preferred embodiment, Takeshita provides an elongated shaft connected at an end to the vibrator body and at the other end to the scaler tip to transmit the vibration generated in the vibrator body to the scaler tip. The shaft is resiliently supported by the casing of the scaler at a point where the node of flexural vibration is located. The vibrator, together with the vibration transmission shaft and the scaler tip, make up a vibration system which undergoes subsonic vibration in response to vibration generated in the vibrator.

Although the air-driven dental scaler of Takeshita is very effective in removing calculus from teeth and enjoys the advantage of being readily connected to the hose from the dental unit interchangeably with the turbine handpieces, the problem which must be overcome in the design of the Takeshita scaler is that it still generates an audible keen sound or noise which is commonly encountered in the various types of air-driven dental scalers.

DISCLOSURE OF THE INVENTION

The primary object of the present invention is to improve the air-driven dental scaler described in U.S. Pat. No. 4,453,919 to Takeshita in such a manner that the noise or audible sound is substantially eliminated or at least reduced by increasing the frequency of vibration to approach the ultrasonic range.

Generally, the delivery pressure of the air compressor incorporated in dental units is regulated by a pressure relief valve. In most dental units, it is a standard practice to regulate the delivery pressure to about 5 kg/cm$^2$ so that the air pressure at the inlet of the turbine handpieces is about 2 kg/cm$^2$. It is often cumbersome for a dentist to alter the delivery pressure of the air compressor each time the turbine handpiece is disconnected from the hose and the dental scaler is connected thereto instead. Therefore, another object of the invention is to provide an air-driven dental scaler which is operable at the rated air pressure of standard dental units and yet is operable without substantially producing an annoying noise.

A further object of the invention is to provide an air-driven dental scaler having an improved scaling capability.

The present invention provides an air-driven dental scaler comprising a tubular casing, a scaler tip disposed adjacent the distal end of the casing, and an air-driven vibrator received in the casing. The vibrator is substantially the same as that described in U.S. Pat. No. 4,453,919 to Takeshita and comprises a rigid vibrator body having a disk-shaped chamber formed therein. A disk-like rotor, slightly smaller in size than the chamber, is received in the chamber for free movement and is rotated by a swirling air stream injected into the chamber through air injection means.

According to the invention, the vibrator is positioned immediately adjacent the distal end of the scaler casing and the scaler tip is mounted directly to the vibrator body without the intervention of a shaft or other member therebetween. The scaler is designed in such a manner that the scaler tip is unsupported by and vibrationally isolated from the casing, to enable the scaler tip to oscillate without interference by the casing.

It has been observed that this arrangement is successful in considerably reducing the audible sound of the dental scaler, without sacrificing the scaling capability thereof. Presumably, this is partly because this arrangement enables the vibration system, consisting of the vibrator and the scaler tip mounted thereto, to vibrate proportionally more in the elastic vibration mode than in the flexural vibration mode, and, more importantly, because the frequency of the flexural vibration is itself substantially increased.

More specifically, the present inventor has found that, unlike the other types of conventional air-driven dental scalers having sleeve-like rotors, as disclosed, for example, in U.S. Pat. No. Re. 29,687, the dental scaler according to the invention and incorporating the air-driven vibrator of Takeshita undergoes two major different modes of vibration, in addition to the small magnitude of torsional vibration mode; the acoustic or elastic vibration imparted to the vibrator body as a result of the rotor striking the wall of the rotor chamber, and the flexural vibration developed in the vibration system including the vibrator and the scaler tip.

The frequency of acoustic vibration, which is believed to be proportional to the rotational speed of the rotor, may be increased by reducing the size of the components of the vibrator, particularly of the rotor, or by increasing the pressure of the compressed air supplied from the dental unit, or by a combination thereof. To reduce the vibrator size will necessarily result in a reduction in the output power or vibratory energy of the vibrator. Nevertheless, because the scaler tip is directly mounted to the vibrator body, the acoustic vibration energy is transmitted straight to the scaler tip without loss, because of the absence of an intervening shaft that would otherwise add an extra length to the vibration system, which would tend to induce in the vibration system an excessive flexural movement that would be apt to absorb the vibratory energy produced by the vibrator. This enables the size of the vibrator to be reduced in such a manner that the frequency of acoustic vibration can be increased to near the ultrasonic range, while retaining the scaling capability of the scaler.

The frequency of flexural vibration of the vibration system is believed to be another important factor in noise reduction. Namely, it is believed that, by directly mounting the scaler tip to the vibrator body according to the invention, the flexural rigidity of the vibration system comprising the scaler tip as mounted to the vibrator body is increased and the effective length of the system is reduced to a greater degree, thereby increasing the frequency of the flexural vibration. In this manner, the frequencies of both the acoustic and flexural modes of vibration may be increased to near the ultrasonic range, thereby suppressing or at least subdueing audible noise that is annoying to the patient.

Obviously, to reduce the size of the vibrator and to reduce the effective length of the vibration system for the purpose of increasing the frequencies of different modes of vibration required for noise reduction will result in a lower output power or vibratory energy of the vibrator, in the first place, and in a reduced amplitude of vibration of the scaler tip, in the second place, which in turn will result in a lower scaling capability of the dental scaler. Thus, the desirability for noise reduction and the necessity for retaining the scaling capability are two opposing requirements, which must be met in designing the air-driven dental scaler according to the invention. In order to provide a satisfactory scaling capability, the vibration system, comprised of the vibrator and the scaler tip as assembled thereto, must be designed such that the scaler tip is oscillated with a maximum amplitude of vibration. Moreover, for the reasons set out hereinbefore, it is desirable that the dental scaler be operable at the rated air pressure of the existing dental units. This limits the air pressure to be supplied to the vibrator.

The present inventor has conducted extensive experiments in an attempt to develop a dental scaler which is operable at the rated pressure of the dental units, without generating annoying audible noise, and yet has a satisfactory scaling capability. As a result, the inventor has empirically discovered the optimal dimensions for the vibrator and the scaler tip required to cause the resonant frequency of the vibration system to match the frequency of the periodic external force by the vibrator, so that the scaler tip is oscillated with a maximum amplitude. Thus, according to the preferred embodiment of the invention, the scaler tip has a length, as measured in a straightened state thereof and exclusive of the threaded portion thereof, of from 30 to 50 mm, preferably about 40 mm. The body of the vibrator, as measured from the center of the rotor chamber to the front end of the body, has an axial length of from 5 to 30 mm, preferably from 10 to 20 mm. The rotor chamber formed in the vibrator body has an inner diameter of from 5.5 to 8.5 mm, preferably about 7 mm, and an axial thickness of from 0.8 to 1.4 mm, preferably about 1.1 mm. The rotor of the vibrator has an outer diameter of from 5.0 to 8.0 mm, preferably about 6.5 mm, and an axial thickness of from 0.4 to 0.8 mm, preferably about 0.65 mm.

BEST MODE FOR CARRYING OUT THE INVENTION

Figure 1:
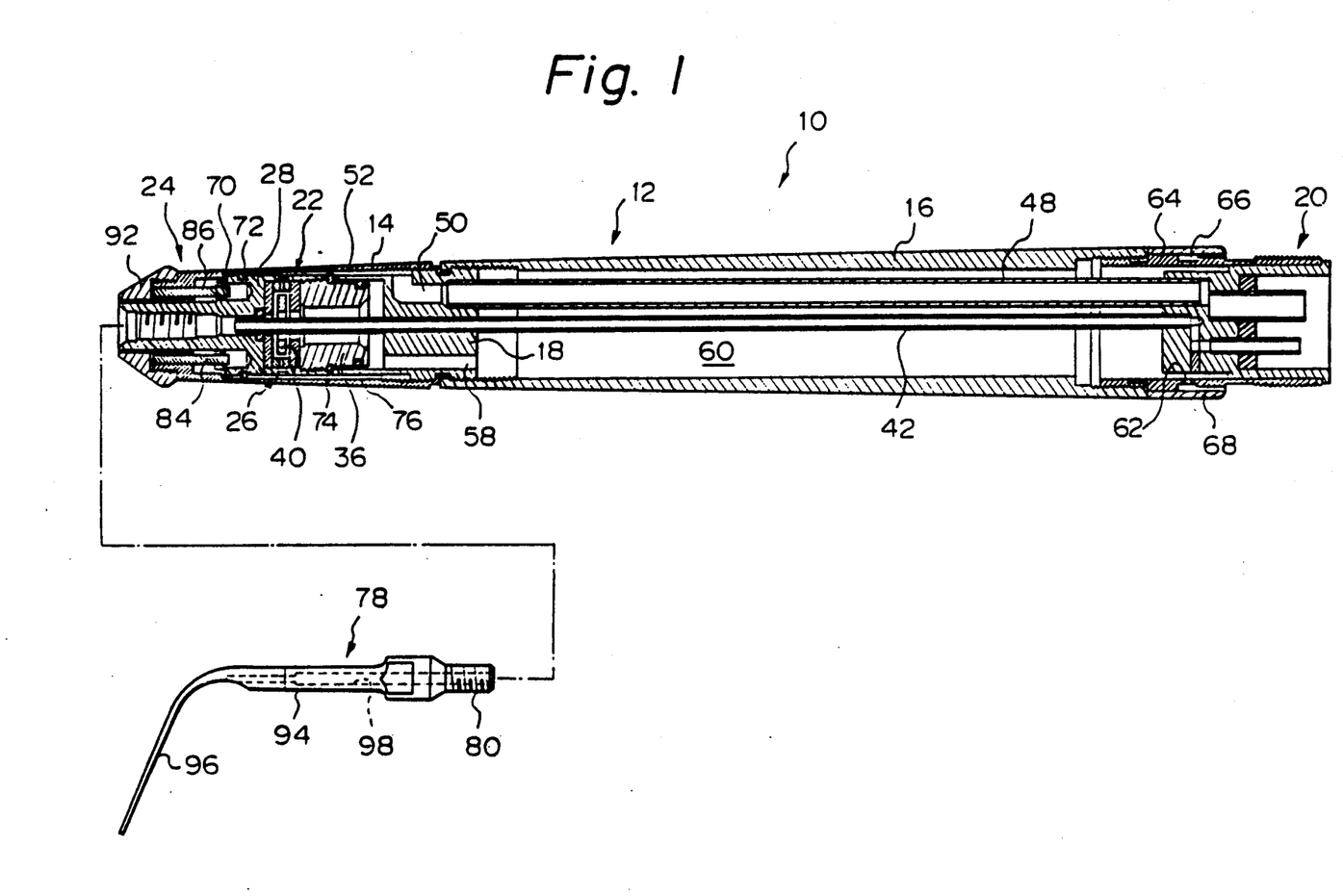
FIG. 1 is an enlarged view, partly in axial cross-section, of the dental scaler according to the invention, with the scaler tip shown as dismounted from the vibrator.

Referring now to the drawings, FIG. 1 illustrates the air-driven dental scaler according to the invention. The dental scaler 10 comprises a tubular casing 12 split into a front section 14 and a rear section 16, which are coupled together by a threaded joint 18. The rear or proximal end 20 of the casing 12 is adapted to be detachably connected by a conventional hose coupling (not shown) to a flexible multiplechannel hose extending from a dental unit. As is well known in the art, the flexible hose has an air passage and a water passage connected, respectively, to a source of compressed air such as an air compressor, with a pressure relief valve, and to a source of water under pressure such as a water pump provided in the dental unit.

An air-driven vibrator 22 in the form of a replaceable cartridge is accommodated within the casing 12 immediately adjacent the distal or front end 24 thereof. The vibrator 22 is the same in principle and operation as that disclosed in U.S. Pat. No. 4,453,919 to Takeshita, the disclosure of which is incorporated by reference herein. The vibrator 22 comprises a vibrator body 26 which is resiliently supported, through elastomeric rings described later, by the casing 12 for vibratory movement with respect thereto. As shown in greater detail in FIG. 2, wherein the vibrator is shown removed from the casing, the vibrator body 26 includes, in the illustrated embodiment, a generally cylindrical recessed housing 28, a pair of side plates 30 and 32 accommodated in the housing 28, a spacer ring or air-ejection ring 34 sandwiched between the side plates, and a backup ring 36 screwed into the housing 28 to air-tightly hold the members 30, 32, and 34 together. The front side plate 30, the intermediate spacer ring 34, and the rear side plate 32 together define a disk-like rotor chamber 38 in which is received a disk-shaped rotor 40 having a size slightly smaller than that of the chamber 38. The edges of the rotor 40 are preferably chamfered as described in U.S. Pat. No. 4,453,919. In the illustrated embodiment, the members 28, 30, 32, 36 and 40 are provided with aligned central apertures for passing a water pipe 42 (FIG. 1) therethrough. The apertures in the rear side plate 32 and the backup ring 36 also serve as exhaust ports for the air exhausted from the chamber 38.

Figure 2:
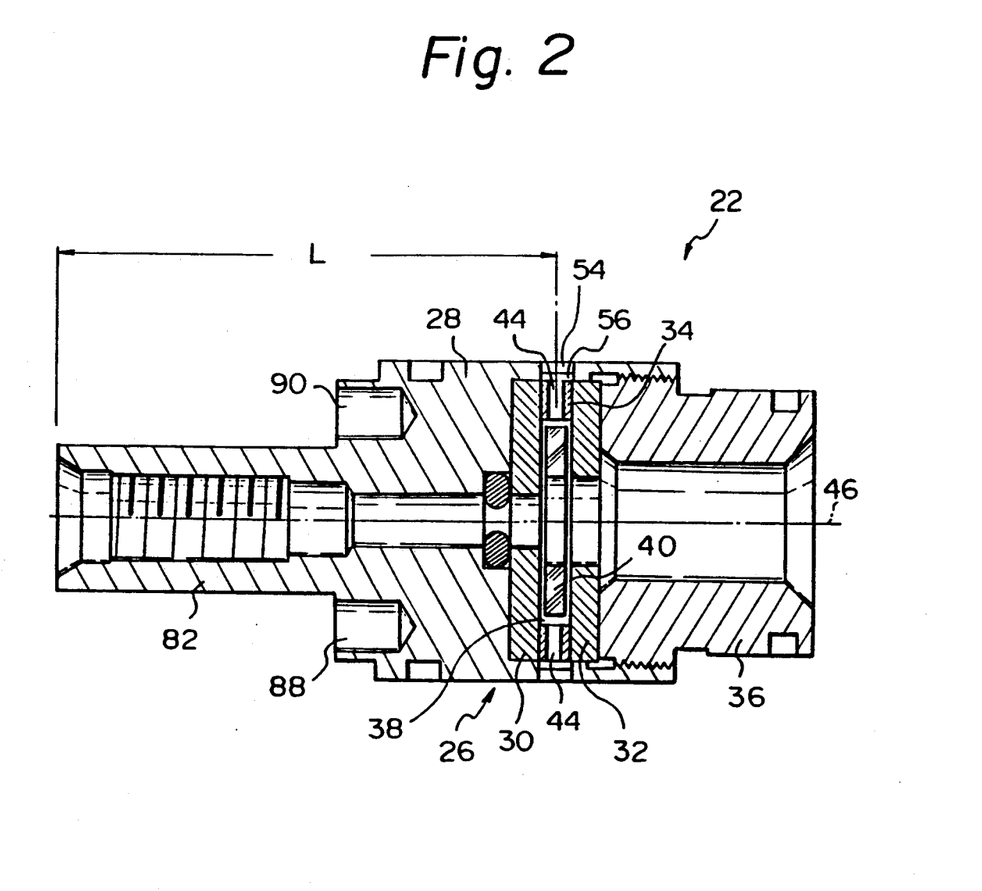
FIG. 2 is an enlarged cross-sectional view of the vibrator.
Figure 3:
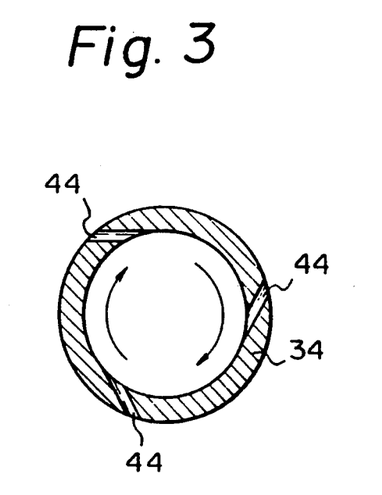
FIG. 3 is an enlarged cross-sectional view of the spacer ring or air ejection ring of the vibrator.

The ejection ring or spacer ring 34 is provided with a plurality of air nozzles 44. Although, for simplicity, these nozzles 44 are shown in FIGS. 1 and 2 as extending in the radial direction, actually they are offset with respect to the axis 46 (FIG. 2) of the chamber 38 as shown in FIG. 3 in such a manner that air under pressure is ejected therethrough substantially tangentially into the chamber 38 to generate a swirling stream of air therein. Compressed air from the dental unit is supplied to the air nozzles 44 through an air pipe 48 (FIG. 1), an air passage 50 in the joint 18, an annular air plenum 52 defined between the casing front piece 14 and the vibrator body 26, radial passages 54 in the housing 28 (FIG. 2), and an annular inner groove 56 formed in the housing 28 and communicated with the nozzles 44. Exhaust air is discharged through the apertures in the rear side plate 32 and the backup ring 36, an exhaust passage 58 in the joint 18, an inner cavity 60 in the casing rear piece 16, radial passages 62 in a hose joint 64 threadingly engaged with the rear piece 16, and an annular passage 66 between the joint 64 and an annular ring 68 (FIG. 1).

As described in U.S. Pat. No. 4,453,919, the swirling air in the chamber 38 causes the rotor 40 to rotate about the axis of the chamber. As the rotor 40 rotates, it wobbles like a coin spinning on a table and strikes the side plates 30 and 32 to impart vibration to the vibrator body 26. Resilient supports such as O-rings 70, 72, 74, and 76 are fitted around the vibrator body 26 to isolate the casing 12 from the vibration induced in the vibrator body 26, and to ensure vibratory movement of the body 26 with respect to the casing.

The vibration generated in the vibrator body 26 is transmitted to a scaler tip 78 mounted to the vibrator body 26. The scaler tip 78 has a threaded portion 80 for connection to a threaded coupling section 82 of the vibrator housing 28. A pair of parallel pins 84 and 86 are provided to prevent the housing 28 from being rotated as the scaler tip 78 is screwed into the housing 28. The front ends of these pins are 84, 86 fixed to the casing front section 14 and the rear ends thereof are engaged through O-rings or elastomeric bushings within corresponding bores 88 and 90 in the housing 28. An end cap 92 is mounted to the casing front piece 14 to conceal the pins 84 and 86 and to provide an abutment or grip for fingers of dentist. In the illustrated embodiment, the scaler tip 78 has a straight shank section 94 and an inclined blade section 96. As the vibrator is operated, the vibration transmitted to the scaler tip causes the blade section 96 to oscillate with any points thereof oscillating along a generally circular or oval trajectory. Upon engagement with tooth surface, the oscillating blade section 96 imparts impact to accumulated calculus and removes it instantaneously from the tooth surface. The scaler tip 78 also has a water passage 98 for receiving a water supply from the water pipe 42. The water flowing out of the passage 98 is pulverized due to oscillation of the blade section 96 and cools the blade and the teeth and washes away the removed debris.

EXAMPLE 1

A dental scaler as shown in FIGS. 1 and 2 was prepared. The rotor chamber 38 had an inner diameter of 7 mm and an axial thickness of 1.1 mm. The rotor 40 had an outer diameter of 6.5 mm and an axial thickness of 0.65 mm, with the diameter of inner aperture being 3.0 mm. The axial length L of the vibrator housing 28, as measured from the center of the rotor chamber to the forwardmost end of the housing 28, was 17.2 mm. All the members of the vibrator body 26 were made from a stainless steel alloy (JIS SUS303). The rotor 40 was made from a high speed steel alloy and was suitably heat treated. The scaler tip 78 had a length of 37 mm in the straightened state, excluding the length of the threaded section 80. The air inlet of the dental scaler was connected to an air compressor and the dental scaler was operated under varying air pressures. The air pressure was measured at the air inlet. The scaler tip was magnetized and the frequency of vibration of the scaler tip was measured by detecting the vibration of the magnetized tip via a magnetic pickup.

Figure 4:
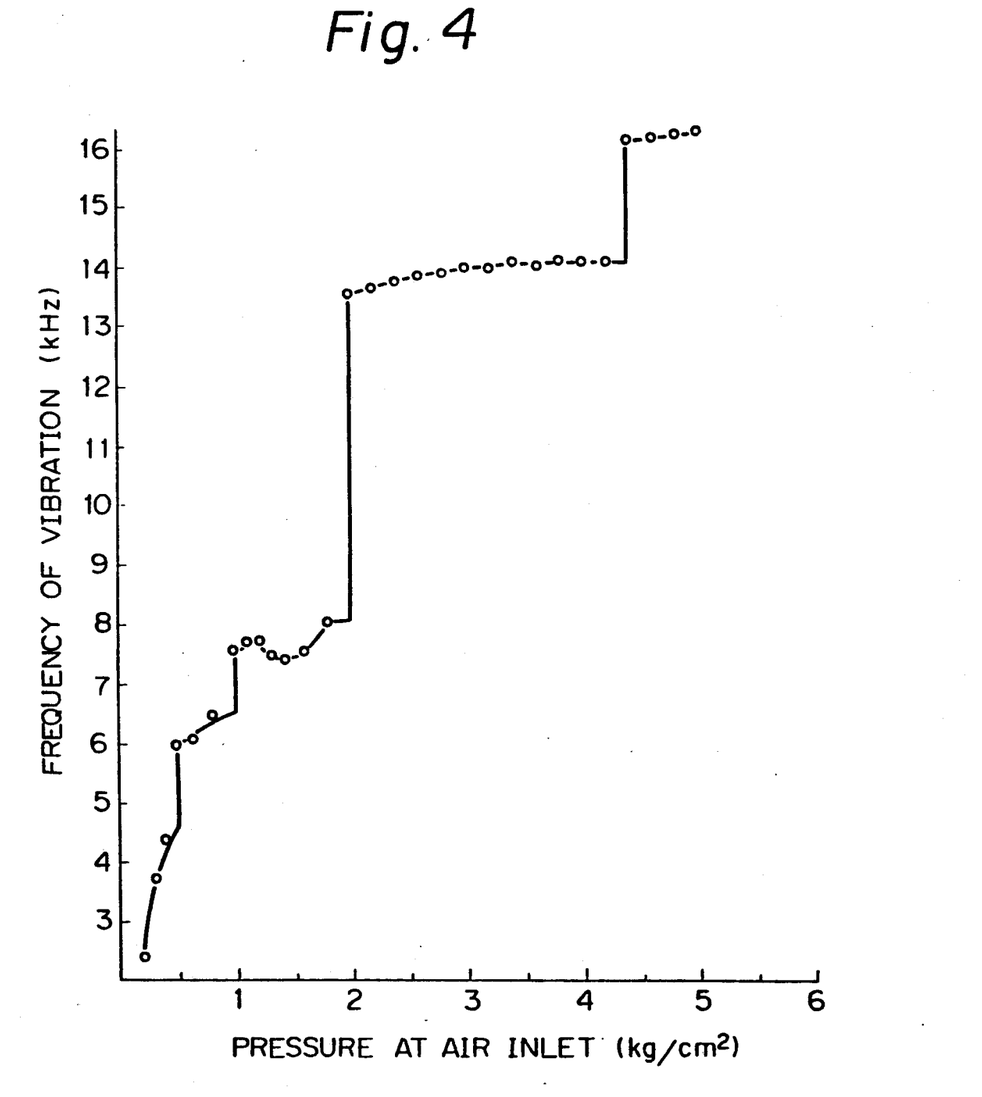
FIG. 4 is a graph showing the results of experiments conducted with the dental scaler according to the invention.

The results were plotted in the graph of FIG. 4, wherein the ordinate represents the frequency of vibration as detected and the abscissa indicates the air pressure at the air inlet of the dental scaler. From the graph, it will be appreciated that the scaler tip vibrates at frequencies roughly equal to or greater than 14 kHz when the air pressure at the air inlet of the dental scaler is greater than about 2 kg/cm$^2$. In this regard, it should be noted that the air pressure as measured at the inlet of the dental scaler is not equal to the supply pressure from the air compressor as regulated by the pressure relief valve. As mentioned hereinbefore, the rated supply pressure suitable to drive a turbine handpieces is about 5 kg/cm$^2$ in a standard dental unit. It is observed that when the dental scaler according to the invention is connected to such a dental unit, the pressure at the air inlet of the dental scaler becomes about 3.5 kg/cm$^2$. Thus, the pressure value of 3.5 kg/cm$^2$ at the inlet of the scaler is equivalent to the rated supply pressure of 5 kg/cm$^2$. According to the graph of FIG. 4, the frequency developed with the inlet air pressure of 3.5 kg/cm$^2$ is about 14 kHz. This means that the dental scaler according to the invention is operable at the rated supply pressure of most dental units to generate vibration having a frequency which is very close to the lower boundary of ultrasonic range, i.e., 15 kHz. In fact, it has been observed that, with the dental scaler according to the invention operated at the rated supply pressure, the only audible sound issuing from the dental scaler was the sound caused by flowing exhaust air. No perceptible level of annoying noise was observed.

The scaling capability of the dental scaler, which is considered to be represented by the amplitude of vibration of the scaler tip, was assessed by observing the formation of mist that resulted from water being pulverized due to high frequency oscillation of the blade section 96 of the scaler tip. Water supplied through the water passage 98 and flowing along the blade section 96 will be pulverized by cavitation if the scaler tip oscillates with an adequate amplitude. When the tested dental scaler was operated under the inlet air pressures of around 3.5 kg/cm$^2$, a good formation of mist was observed. This means that the dental scaler according to the invention exhibits a satisfactory scaling capability.

Figure 5:
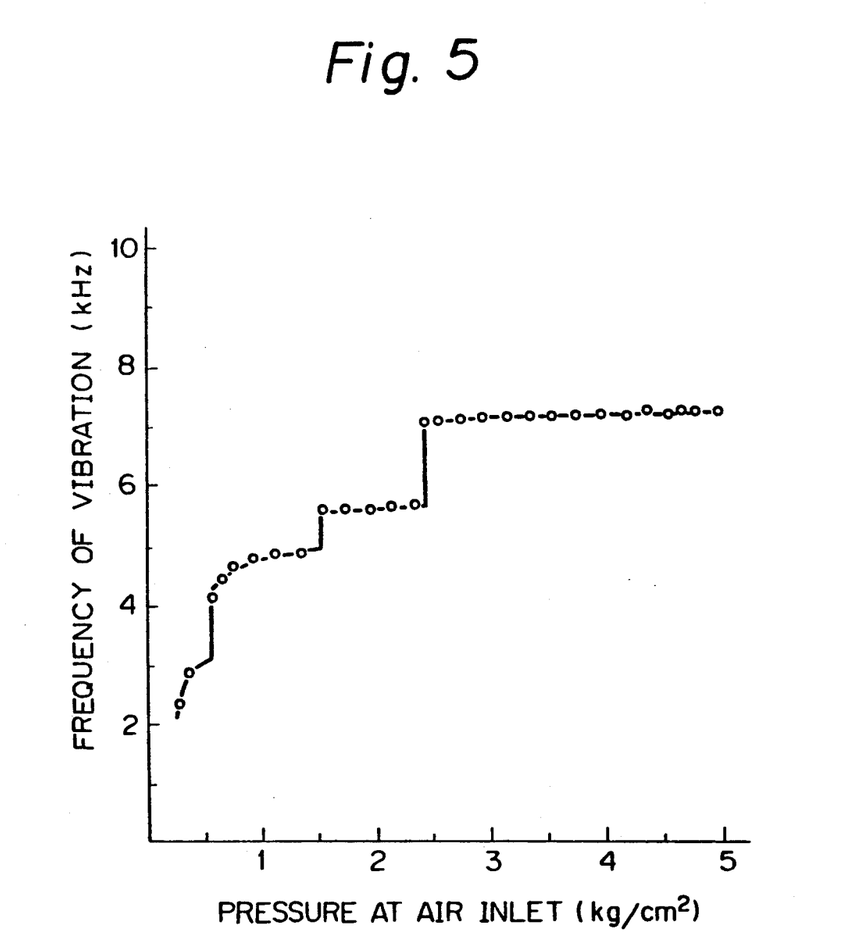
FIG. 5 is a graph showing the results of experiments conducted with a dental scaler developed by Takeshita.

For comparison, the dental scaler of Takeshita as shown in FIG. 3 of U.S. Pat. No. 4,453,919 was tested. The rotor chamber of the vibrator had an inner diameter of 7 mm and an axial thickness of 1.8 mm. The rotor had an outer diameter of 6.5 mm and an axial thickness of 1.1 mm. A similar scaler tip was used and the vibration was measured in a similar manner by making use of the same magnetic pickup. The results are plotted in the graph of FIG. 5. As shown, the frequency of vibration of this dental scaler was at maximum about 7 kHz, which is far lower than the ultrasonic range.

EXAMPLE 2

Figure 6:
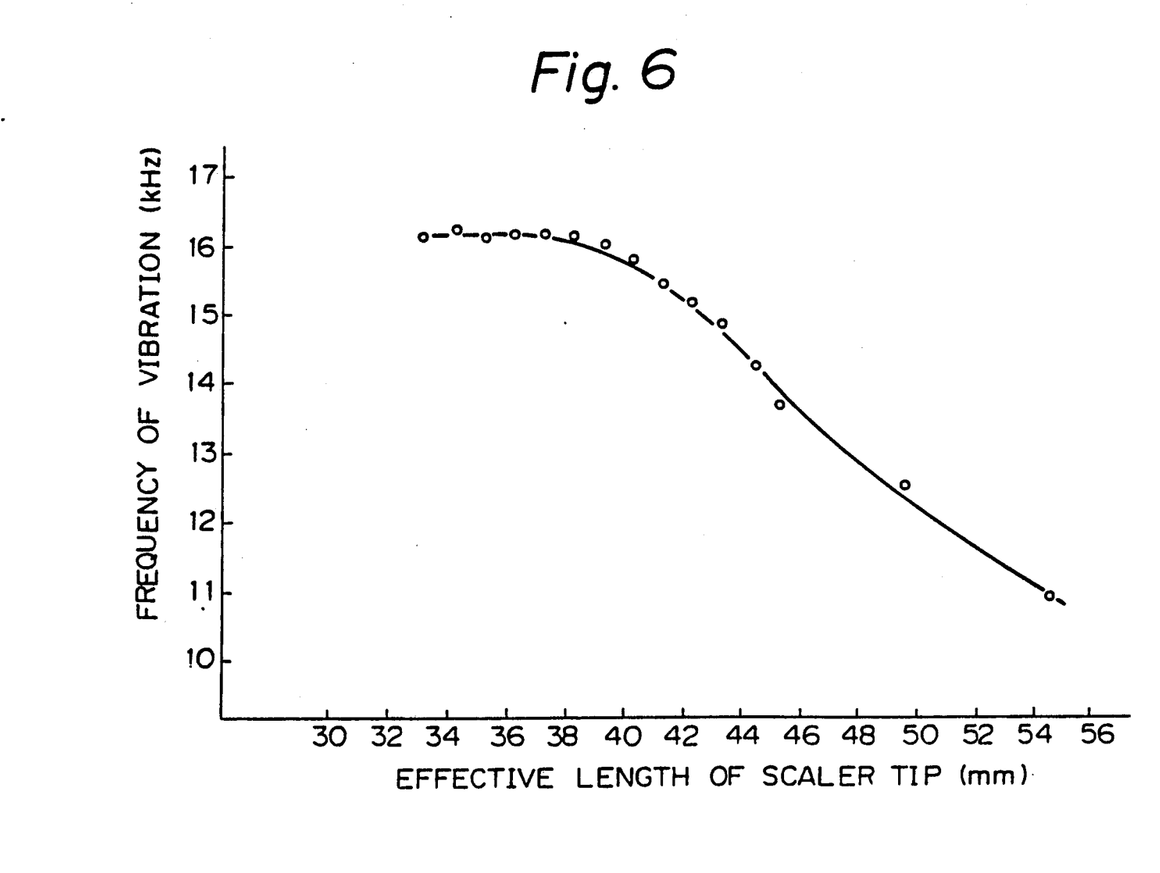
FIG. 6 is a graph showing the variation in the frequency of vibration for varying lengths of the scaler tip mounted to the vibrator shown in FIG. 2.

A plurality of straight scaler tips having different length were prepared. The effective length of the scaler tips, exclusive of the threaded section, varied from about 30 to 54 mm. These scaler tips were mounted to the dental scaler of Example 1 and the scaler was operated under an inlet air pressure of 3.5 kg/cm$^2$. The frequency of vibration of the various scaler tips was measured in the same manner as in Example 1 and the results are plotted in the graph of FIG. 6. As shown, the dental scaler with scaler tips having effective lengths of from 33 to 40 mm operated at a frequency of vibration equal to or greater than 16 kHz. With the scaler tips having the effective length shorter than 33 mm, measurement was not possible because the amplitude of vibration was too small to be detected by the magnetic pickup.

EXAMPLE 3

Figure 7:
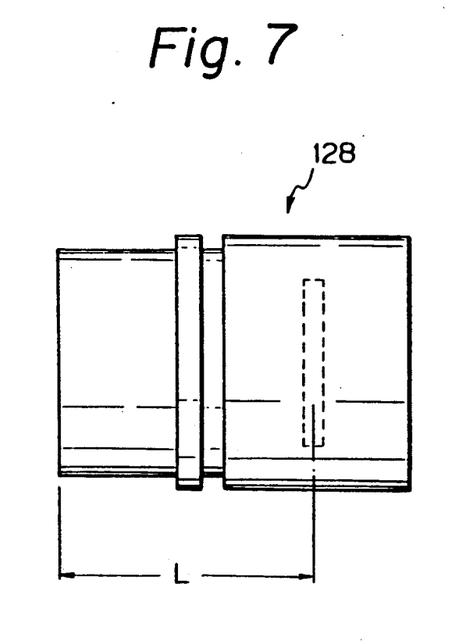
FIG. 7 is an enlarged view showing another vibrator housing of the dental scaler according to the invention.
Figure 8:
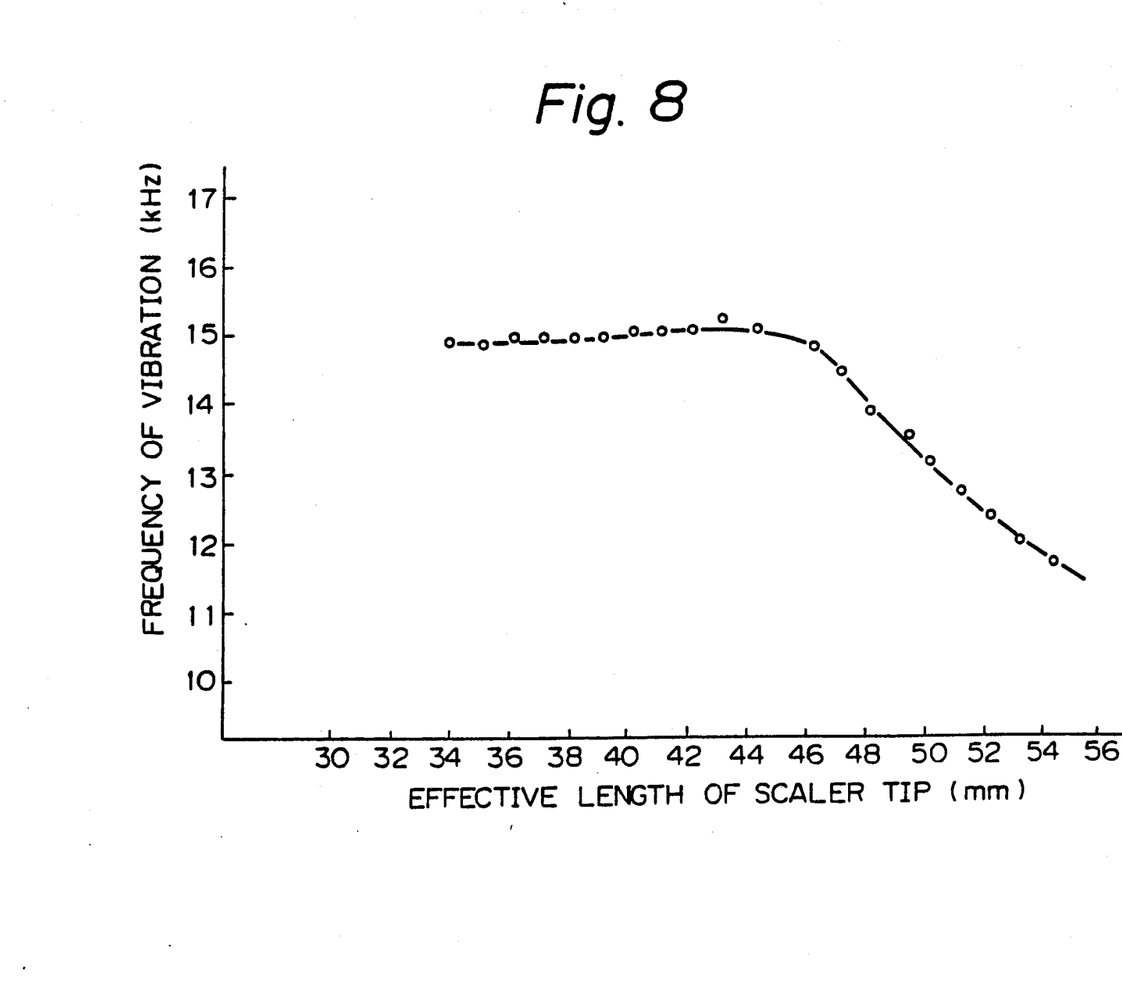
FIG. 8 is a graph showing the variation in the frequency of vibration for varying lengths of the scaler tip mounted to the vibrator housing of FIG. 7.

Another vibrator having a vibrator housing shown in FIG. 7 was prepared. The housing 128 of FIG. 7 differed from the housing 28 of FIG. 2 in that the threaded coupling section for mounting the scaler tip was enlarged and stubbed and that the axial length L, as measured from the center of rotor chamber to the front end of the housing was 11.0 mm. Other components of the vibrator were the same as those used in Example 1. Thus, the sizes of the rotor chamber and the rotor were the same as those of Example 1. The assembled vibrator was mounted within a casing similar to that shown in FIG. 1 and the scaler tips used in Example 2 were mounted thereto. The dental scaler was operated and tested in the same manner as in Example 2. The results are shown in the graph of FIG. 8. It will be noted that, with the scaler tips having an effective length varying from 34 to 46 mm, the frequency of vibration generated by the dental scaler was about 15 kHz. With the scaler tips having an effective length shorter than 34 mm, the amplitude of vibration was too small to enable frequency measurement.

While the present invention has been described herein particularly with relation to an air-driven dental scaler, it is contemplated that the present invention is not limited thereby. For example, the present invention is also applicable to air-driven dental instruments for condensing amalgam or for removing crown or other implants from teeth. In these situations, the scaler tip 78 may be replaced with a suitable tool such as a crown remover or an amalgam condenser.

I claim:

1. An air-driven dental scaler comprising:
  a tubular casing adapted to be held by an operator and having a proximal end and a distal end, a scaling tool disposed adjacent said distal end of the casing, an air-driven vibrator received in said casing and resilient support means for supporting said vibrator within said casing and for isolating the casing from the vibration induced by said vibrators,
  said air-driven vibrator comprising a housing defining a cylindrical chamber having a pair of opposite end faces, a vibration generating element loosely held within said chamber, and means for passing fluid through said chamber to cause said element to alternately strike said end faces to thereby generate vibration, said chamber being axially aligned with the longitudinal axis of said casing, the axial length of said chamber being less than its diameter; and
  said vibrator being positioned immediately adjacent said distal end and vibrationally coupled to said scaling tool in a vibration transmitting relationship thereto, said vibrator and said scaling tool as coupled together being vibrationally isolated from said casing so that the vibration generated in said vibrator by the striking action of said element is transmitted to the scaling tool more in an acoustic vibration mode than in a flexural vibration mode.

2. An air-driven dental scaler as set forth in claim 1, wherein said vibrator comprises coupling means for connecting said scaling tool directly to the vibrator and said coupling means is substantially unsupported by and vibrationally isolated from said casing.

3. An air-driven dental scaler as set forth in claim 2, wherein said coupling means comprises a threaded coupling.

4. A dental scaler in accordance with claim 1 wherein said scaling tool has a first threaded portion and said casing has a second threaded portion for receiving said first threaded portion thereby directly coupling said scaling tool to said casing.

5. A dental scaler in accordance with claim 4 wherein said second threaded portion is a threaded coupling which terminates at a point approximately even with said distal end of said casing.

6. A dental scaler in accordance with claim 1 wherein said scaling tool vibrates at about 14 KHz or more with an air input to the scaler of 2 kg/cm$^2$ to 5 kg/cm$^2$.

7. An air-driven dental scaler as set forth in claim 1, wherein said element is a disk having an outer diameter of from 5.0 to 8.0 mm and a thickness of from 0.4 to 0.8 mm.

8. An air-driven dental scaler as set forth in claim 1, wherein said chamber has an inner diameter of from 5.5 to 6.5 mm and an axial thickness of 0.6 to 1.4 mm.

9. An air-driven dental scaler as set forth in claim 1, wherein said vibrator housing has an axial length L, as measured from the center of said chamber to the forwardmost end of said housing, of from 5 to 30 mm.

10. An air-driven dental scaler as set forth in claim 9, wherein said axial length L of said housing is from 10 to 20 mm.

11. An air-driven dental scaler as set forth in claim 1, wherein said scaling tool has an effective length, as measured in a straightened state thereof, of from 30 to 50 mm.

12. The dental scaler of claim 1, wherein said resilient support means consists of one or more resilient O-rings which provide the only radial support between said vibrator housing and said casing and wherein no radial support is provided between said scaling tool and said casing.

13. An air-driven dental scaler in accordance with claim 1 which vibrates said scaling tool at about 14 KHz or more with an air input to the vibrator of 2–5 Kg/cm$^2$.

14. An air-driven dental scaler comprising:
  a tubular casing adapted to be held by an operator and having a proximal end and a distal end, a scaling tool disposed adjacent said distal end of the casing, and an air-driven vibrator received in said casing;
  said air-driven vibrator comprising a housing defining a cylindrical chamber having a pair of opposite end faces, a vibration generating element loosely held within said chamber, and means for passing fluid through said chamber to cause said element to alternately strike said end faces to thereby generate vibration, said chamber being axially aligned with the longitudinal axis of said casing, the axial length of said chamber being less than its diameter;
  said vibrator being positioned immediately adjacent said distal end and vibrationally coupled to said scaling tool without intervention of a shaft that would vibrate in a flexural vibration mode, said vibrator and said scaling tool as coupled with each other being vibrationally isolated from said casing.

15. An air-driven dental scaler as set forth in claim 14, wherein the vibration generated in said vibrator by the striking action of said element is transmitted to said scaling tool more in acoustic vibration mode than in a flexural vibration mode.

16. An air-driven dental scaler as set forth in claim 14, wherein said scaling tool is vibrated at about 14 KHz or more with an air input to the vibrator of 2–5 kg/cm$^2$.

17. The dental scaler of claim 14 further comprising resilient support means for vibrationally isolating said vibrator an said scaling tool from said casing, wherein said resilient support means consists of one or more resilient O-rings which provide the only radial support between said vibrator housing and said casing and wherein no radial support is provided between said scaling tool and said casing.

18. An air-driven dental vibratory instrument comprising:
  a tubular casing adapted to be held by an operator and having a proximal end and a distal end, a dental tool disposed adjacent said distal end of the casing, and an air-driven vibrator received in said casing;
  said air-driven vibrator comprising a housing defining a cylindrical chamber having a pair of opposite end faces, a vibration generating element loosely held within said chamber, and means for passing air under pressure through said chamber to cause said element to alternately strike said end faces to thereby generate vibration, said chamber being axially aligned with the longitudinal axis of said casing, the axial length of said chamber being less than its diameter;

said vibrator being positioned immediately adjacent said distal end and vibrationally coupled to said dental tool in a vibration transmitting relationship thereto, said vibrator and said dental tool as coupled together being vibrationally isolated from said casing in such a manner that the vibration generated in said vibrator by the striking action of said element is transmitted to said dental tool more in an acoustic vibration mode than in a flexural vibration mode.

19. The air-driven dental vibratory instrument of claim 18 further comprising resilient support means for vibrationally isolating said vibrator and said dental tool from said casing, wherein said resilient support means consists of one or more resilient O-rings which provide the only radial support between said vibrator housing and said casing and wherein no radial support is provided between said dental tool and said casing.

20. An air-driven vibratory instrument in accordance with claim 18 which vibrates said dental tool at about 14 KHz or more with an input to the vibrator of 2-5 Kg/cm$^2$.

21. An air-driven dental vibratory device comprising:
a tubular casing adapted to be held by an operator and having a proximal end and a distal end, a working tool disposed adjacent said distal end of the casing for engagement with a tooth, and an air-driven vibrator received in said casing;

said air-driven vibrator comprising a housing defining a cylindrical chamber having a pair of opposite end faces, a vibration generating element loosely held within said chamber, and means for passing air under pressure through said chamber to cause said element to alternatively strike said end faces to thereby generating vibration, said chamber being axially aligned with the longitudinal axis of said casing, the axial length of said chamber being less than its diameter;

said vibrator being positioned immediately adjacent said distal end and vibrationally coupled to said working tool in a vibration transmitting relationship thereto, said vibrator and said working tool as coupled with each other being vibrationally isolated from said casing in such a manner that the vibration generated in said vibrator by the striking action of said element is transmitted to said working tool more in an acoustic vibration mode than in a flexural vibration mode.

22. The air-driven dental vibratory device of claim 21 further comprising resilient support means for vibrationally isolating said vibrator and said working tool from said casing, wherein said resilient support means consists of one or more resilient O-rings which provide the only radial support between said vibrator housing and said casing and wherein no radial support is provided between said working tool and said casing.

23. An air-driven dental vibratory instrument in accordance with claim 21 which vibrates said working tool at about 14 KHz or more with an input to the vibrator of 2-5 Kg/cm$^2$.

24. An air-driven dental vibratory device for driving a dental working tool comprising:
a tubular casing adapted to be held by an operator and having a proximal end and a distal end of the casing, and an air-driven vibrator received in said casing;

said air-driven vibrator comprising a housing defining a cylindrical chamber having a pair of opposite end faces, a vibration generating element loosely held within said chamber, and means for passing air under pressure through said chamber to cause said element to alternately strike said end faces to thereby generate vibration, said chamber being axially aligned with the longitudinal axis of said casing, the axial length of said chamber being less than its diameter;

said vibrator being positioned immediately adjacent said distal end, said vibratory device comprising means for coupling the dental working tool directly to said vibrator housing without intervention of a shaft that would vibrate in a flexural vibration mode to transfer vibration generated in said vibrator to the working tool more in an acoustic vibration mode than in a flexural vibration mode, said device further comprising means for vibrationally isolating said vibrator and the working tool from said casing.

25. The air-driven dental vibratory device of claim 24 further comprising resilient support means for vibrationally isolating said vibrator and the dental tool from said casing, wherein said resilient support means consists of one or more resilient O-rings which provide the only radial support between said vibrator housing and said casing and wherein no radial support is provided between the dental tool and said casing.

26. An air-driven dental vibratory instrument in accordance with claim 24 which vibrates the dental working tool at about 14 KHz or more with an input to the vibrator of 2-5 Kg/cm$^2$.

* * * * *

UNITED STATES PATENT AND TRADEMARK OFFICE
CERTIFICATE OF CORRECTION

PATENT NO. : 5,190,456

DATED : March 2, 1993

INVENTOR(S) : SAKAKIBARA et al

It is certified that error appears in the above-identified patent and that said Letters Patent is hereby corrected as shown below:

Col. 9, line 64, "0.6" should read --0.8--.

Col. 11, line 39, "generating" should read --generate--.

Signed and Sealed this

Eleventh Day of January, 1994

*Attest:*

BRUCE LEHMAN

*Attesting Officer*     *Commissioner of Patents and Trademarks*